(12) United States Patent
Abdelgany

(10) Patent No.: US 7,488,331 B2
(45) Date of Patent: Feb. 10, 2009

(54) ORTHOPEDIC IMPLANT BENDER

(75) Inventor: Mahmoud F. Abdelgany, Rockaway, NJ (US)

(73) Assignee: Custon Spine, Inc., Parsippany, NJ (US)

( * ) Notice: Subject to any disclaimer, the term of this patent is extended or adjusted under 35 U.S.C. 154(b) by 182 days.

(21) Appl. No.: 11/280,013

(22) Filed: Nov. 16, 2005

(65) Prior Publication Data

US 2006/0264973 A1 Nov. 23, 2006

Related U.S. Application Data

(60) Provisional application No. 60/683,747, filed on May 23, 2005.

(51) Int. Cl.
*A61F 11/00* (2006.01)
*B21J 13/08* (2006.01)

(52) U.S. Cl. ........................................ 606/109; 72/458

(58) Field of Classification Search .................... 72/213, 72/389.1, 390.4, 458, 479, 216, 217, 409.1, 72/388, 154, 459; 606/109; 140/106
See application file for complete search history.

(56) References Cited

U.S. PATENT DOCUMENTS

| | | | | |
|---|---|---|---|---|
| 4,373,373 A | * | 2/1983 | Schaefer | 72/413 |
| 4,716,757 A | * | 1/1988 | McGregor et al. | 72/387 |
| 5,113,685 A | | 5/1992 | Asher et al. | |
| 5,161,404 A | * | 11/1992 | Hayes | 72/458 |
| 5,389,099 A | | 2/1995 | Hartmeister et al. | |
| 5,490,409 A | * | 2/1996 | Weber | 72/458 |
| 5,548,985 A | | 8/1996 | Yapp | |
| 5,564,302 A | | 10/1996 | Watrous | |
| 5,651,283 A | * | 7/1997 | Runciman et al. | 72/390.4 |
| 6,006,581 A | | 12/1999 | Holmes | |
| 6,035,691 A | | 3/2000 | Lin et al. | |
| 6,644,087 B1 | | 11/2003 | Ralph et al. | |
| 2006/0150698 A1 | * | 7/2006 | Garner et al. | 72/31.04 |

* cited by examiner

*Primary Examiner*—Pedro Philogene
(74) *Attorney, Agent, or Firm*—Rahman LLC

(57) ABSTRACT

An orthopedic implant bender comprising a first and second side each comprising a curved body comprising a handle end and an implant receiving end, wherein the implant receiving end comprises a first and second hole, wherein the second hole receives an implant longitudinal member; a cam connected to the implant receiving end and capable of fitting into the first hole, wherein the cam comprises an indented middle section and two ends each having a peg extending therefrom; a base connected to the handle end; and a lever connected to the cam and rotatable with respect to the body, wherein the lever comprises a pair of arms spaced apart to accommodate a width of the implant receiving end of the body; and a pair of through holes in each of the arms capable of attaching to the pegs of the cam, wherein rotation of the lever causes rotation of the cam.

20 Claims, 12 Drawing Sheets

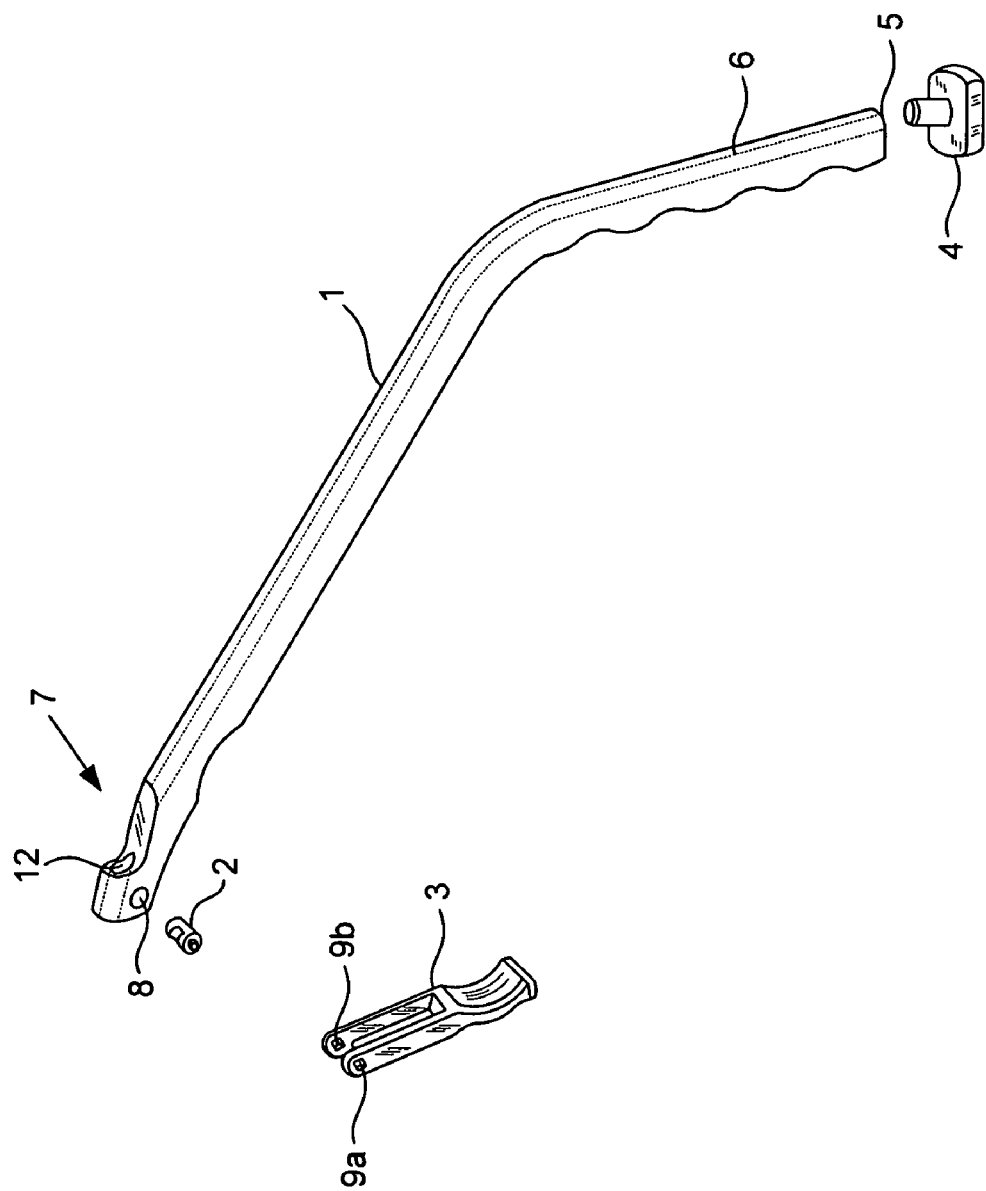

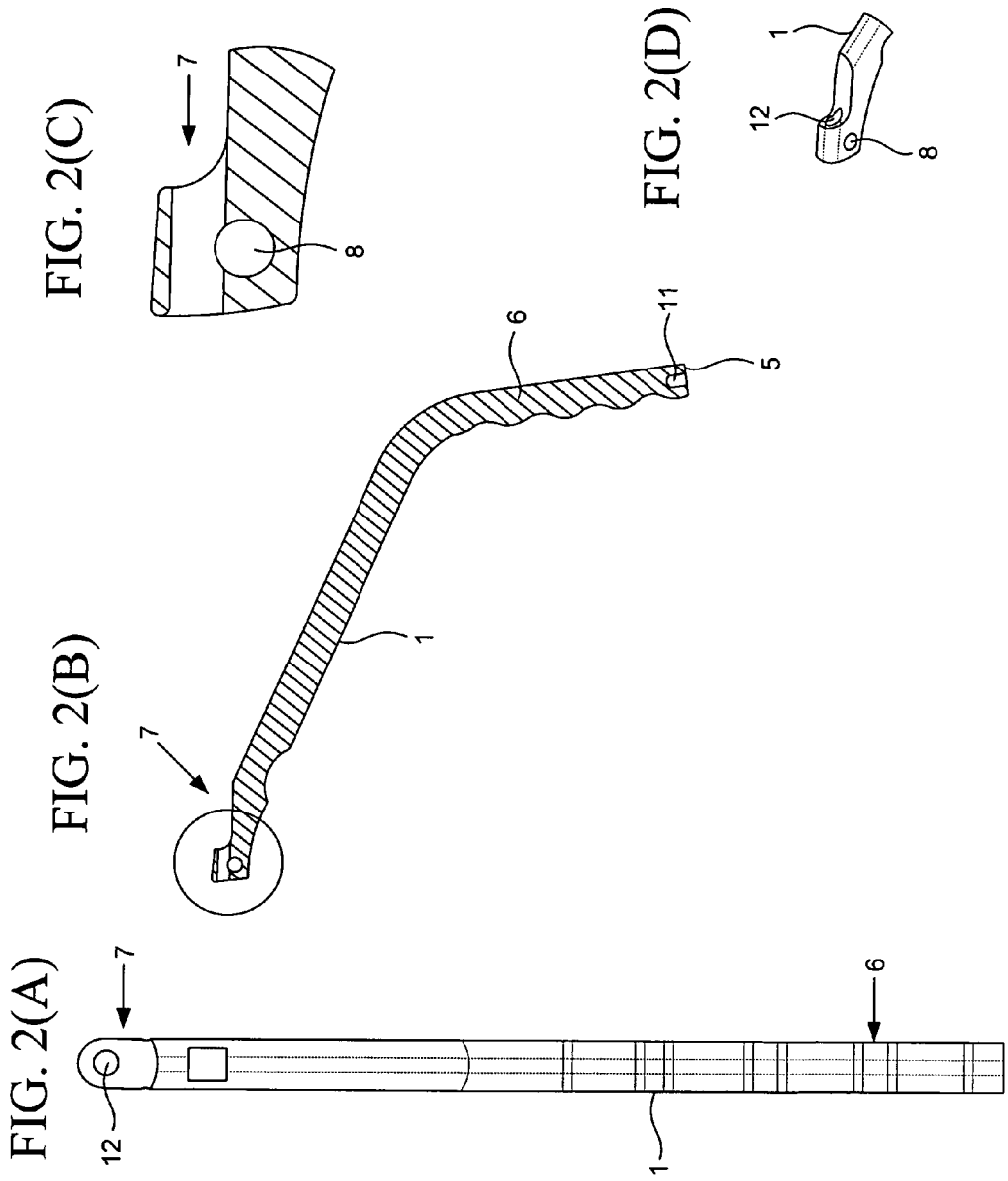

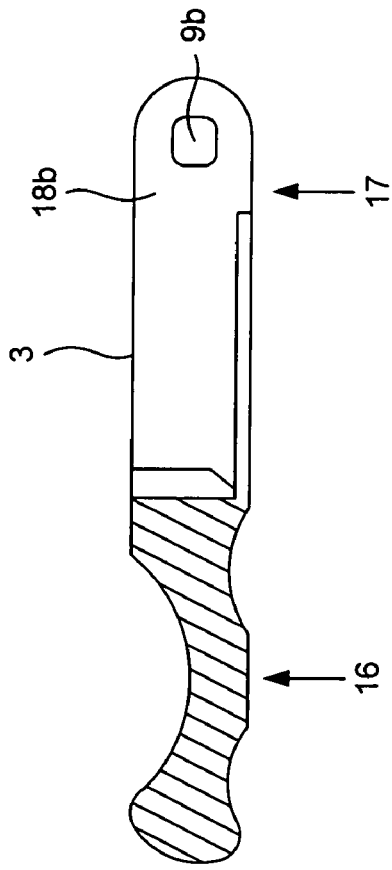
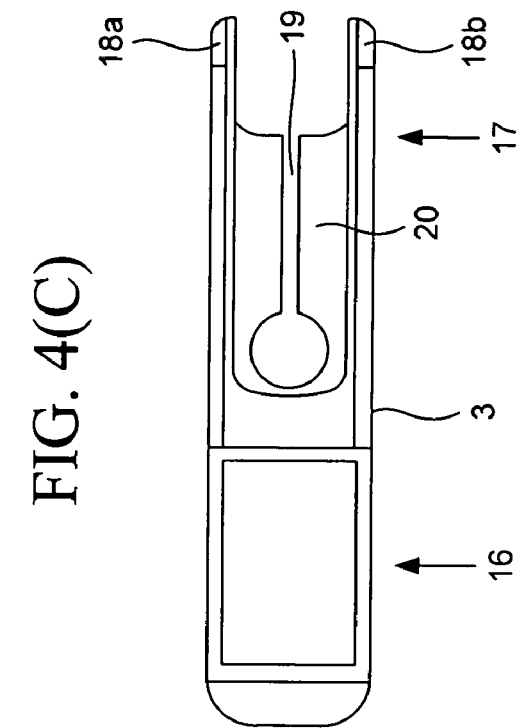
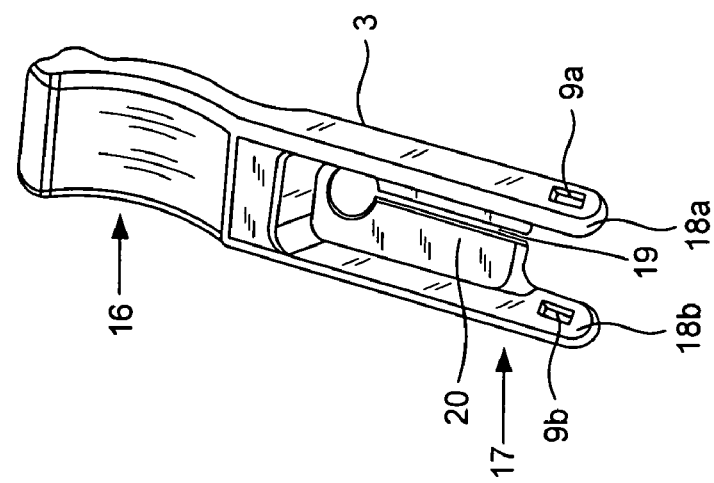
FIG. 4(B)
FIG. 4(C)
FIG. 4(A)

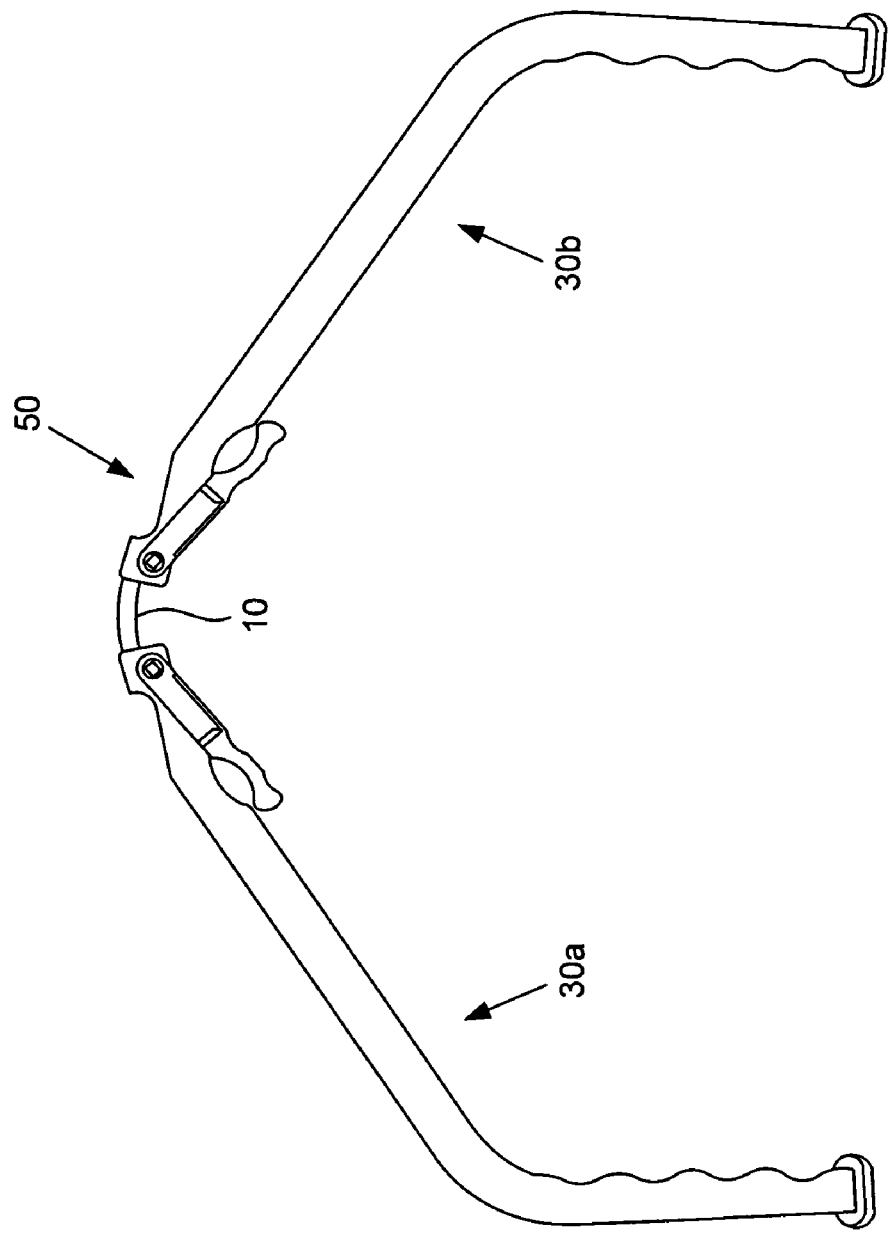

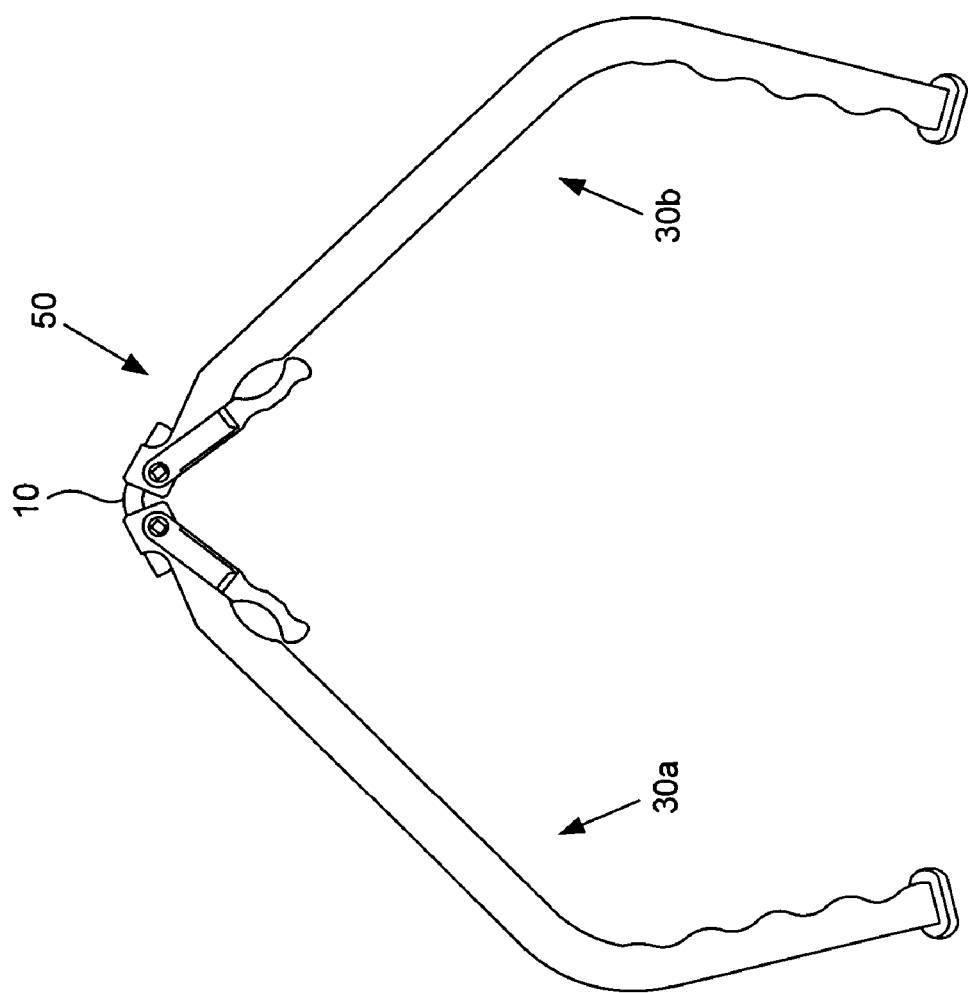

ORTHOPEDIC IMPLANT BENDER

CROSS-REFERENCE TO RELATED APPLICATION

This application claims the benefit of U.S. Provisional Patent Application No. 60/683,747 filed on May 23, 2005, the contents of which, in its entirety, is herein incorporated by reference.

BACKGROUND

1. Field of the Invention

The embodiments herein generally relate to medical devices, and, more particularly, to devices used to manipulate a rod into a proper shape for use in spinal surgeries.

2. Description of the Related Art

Generally, most conventional rod or plate benders used in orthopedic surgery fall into two categories: (1) big heavy table top models, and (2) portable models that generally do not provide significant leverage and are often difficult to use. Various conventional devices are typically too bulky, heavy, expensive, and difficult to use. Additionally, most conventional devices typically only provide minimal leverage and tend to require significant effort from the user. Furthermore, some conventional devices may not be able to accommodate different size implants within one set of instruments. Therefore, there remains a need for a novel rod bender device that is capable of overcoming the limitations of the conventional devices.

SUMMARY

In view of the foregoing, an embodiment provides an orthopedic implant bender comprising a first side and a second side, wherein each of the first side and the second side comprises a curved body member comprising a handle end and an implant receiving end; a cam member rotatably connected to the implant receiving end of the body member; and a lever connected to the cam member and rotatable with respect to the body member, wherein the lever comprises a pair of generally parallel arms sufficiently spaced apart to accommodate a width of the implant receiving end of the body member, wherein rotation of the lever causes rotation of the cam member. Preferably, the implant receiving end comprises a first hole and a second hole, the first hole being transverse to the second hole. Moreover, the second hole is preferably dimensioned and configured to receive an implant longitudinal member. Furthermore, the cam member is preferably dimensioned and configured to fit into the first hole of the implant receiving end of the body member. The cam member may comprise an indented middle section and a peg extending from each distal longitudinal end of the cam member. Additionally, the lever may further comprise a pair of through holes in each of the arms, the through holes being dimensioned and configured to attach to the peg extending from each distal longitudinal end of the cam member. Also, the indented middle section of the cam member is preferably dimensioned and configured to engage the implant longitudinal member. Preferably, a curved configuration of the body member requires a minimal force to be applied to the handle end of the body member in order to bend the implant longitudinal member. The implant bender may further comprise a base member connected to the handle end of the body member. Preferably, the arms are flexible with respect to one another. Furthermore, the lever may comprise a wall connecting the arms to each other, wherein the wall comprises a slit. Additionally, the lever may further comprise a contoured end positioned opposite to the arms.

Another embodiment provides an orthopedic implant bender comprising a first side and a second side, wherein each of the first side and the second side comprises a curved body member comprising a handle end and an implant receiving end, wherein the implant receiving end comprises a first hole and a second hole, the first hole being transverse to the second hole, and wherein the second hole is dimensioned and configured to receive an implant longitudinal member; a screw-like member connected to the implant receiving end of the body member; and a handle connected to the screw-like member and rotatable with respect to the body member, wherein rotation of the handle causes rotation of the screw-like member. Preferably, the screw-like member is dimensioned and configured to fit into the first hole of the implant receiving end of the body member. The implant bender may further comprise a base member connected to the handle end of the body member. Furthermore, the first hole is preferably dimensioned and configured to engage the screw-like member. Preferably, the handle end is substantially transverse to the implant receiving end. Additionally, a curved configuration of the body member preferably requires a minimal force to be applied to the handle end of the body member in order to bend the implant longitudinal member.

Another embodiment provides a method of bending an implant longitudinal member in an orthopedic implant bender comprising a first side and a second side, wherein each of the first side and the second side comprises a curved body member comprising a handle end and an implant receiving end, wherein the implant receiving end comprises a first hole and a second hole; a cam member rotatably connected to the body member; and a lever connected to the cam member; wherein the method comprises inserting the implant longitudinal member in the second hole; rotating the lever with respect to the body member, wherein rotation of the lever causes rotation of the cam member; locking the implant longitudinal member in the second hole; and squeezing together the handle ends of the first and second sides of the orthopedic implant bender, wherein the squeezing causes the implant longitudinal member to bend, wherein a curved configuration of the body member preferably requires a minimal force to be applied to the handle end of the body member in order to bend the implant longitudinal member.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 1 illustrates an exploded view of one side of a rod bender device according to an embodiment herein;

FIGS. 2(A) through 2(D) illustrate schematic diagrams of the rod bender body of the rod bender device of FIG. 1 according to an embodiment herein;

FIGS. 4(A) through 4(C) illustrate schematic diagrams of the rod bender lever of the rod bender device of FIG. 1 according to an embodiment herein;

FIGS. 6(A) through 6(C) illustrate schematic diagrams of a rod bender device manipulating a rod according to an embodiment herein;

DETAILED DESCRIPTION OF PREFERRED EMBODIMENTS

Figure 3A:
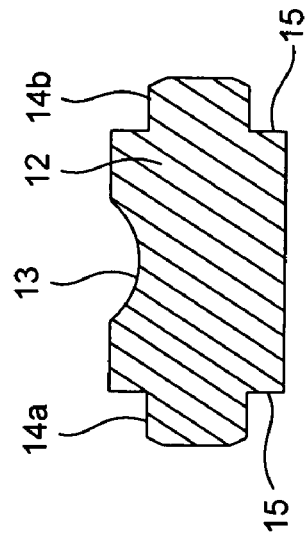
FIGS. 3(A) through 3(D) illustrate schematic diagrams of the rod bender cam of the rod bender device of FIG. 1 according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a novel rod bender device that is capable of overcoming the limitations of the conventional devices. The embodiments herein achieve this by providing a rod bender with enhanced geometry and leverage to optimize physical human efforts in contouring of an orthopedic implant. The embodiments herein can be used to contour a metallic implant during an orthopedic and/or spine surgery. Referring now to the drawings, and more particularly to FIGS. 1 through 9, there are shown preferred embodiments.

Figure 6A:
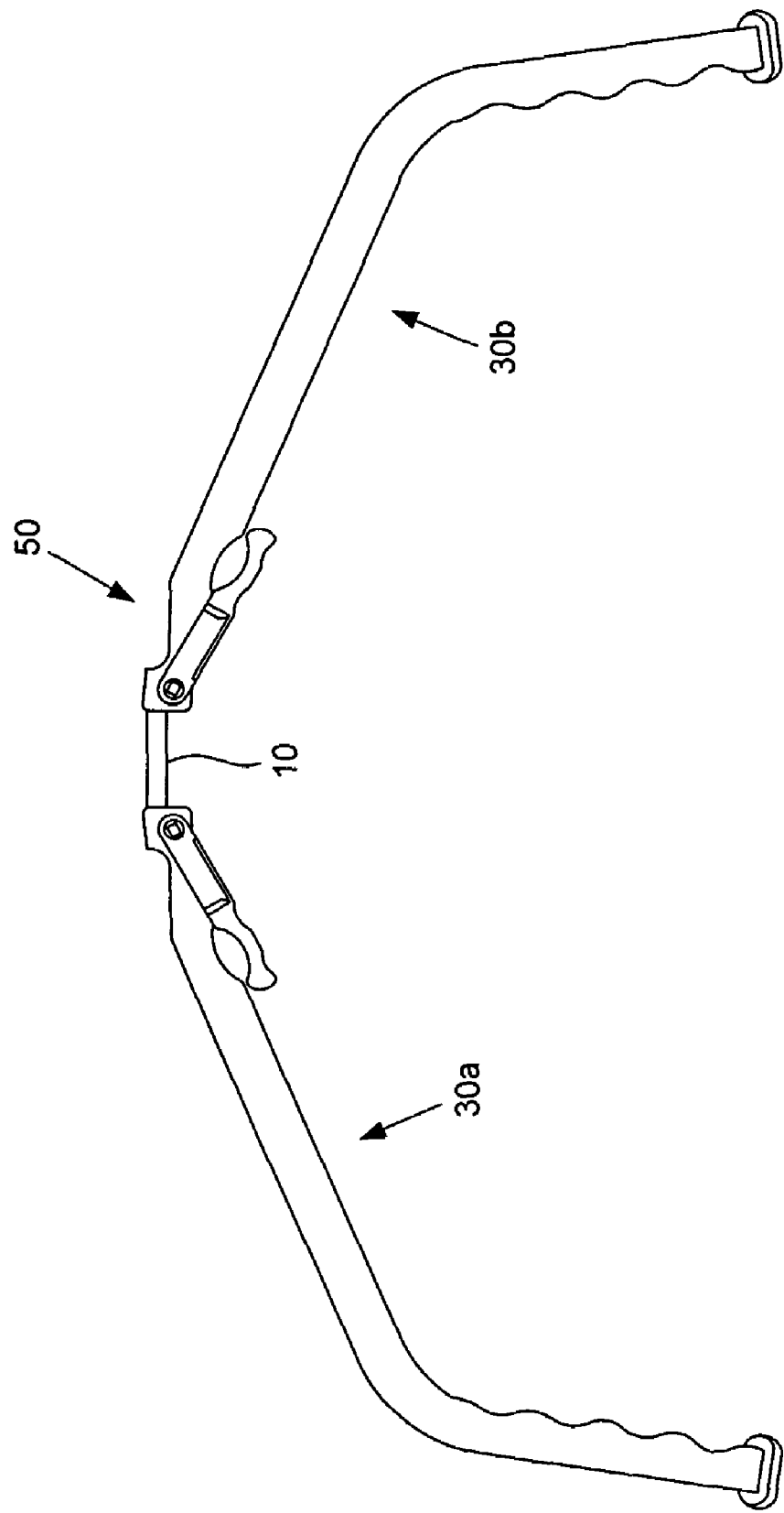

FIGS. 1 and 6(A) through 6(C) illustrate a view of a rod bender device 50 according to an embodiment herein, with FIG. 1 illustrating one side of the rod bender device 50, and with FIGS. 6(A) through 6(C) illustrating a left side 30a and right side 30b of the rod bender device 50. Generally, each side 30a, 30b of the rod bender device 50 comprises a body 1, a cam 2, a lever 3, and a base 4. The body member 1 comprises a handle end 6 positioned substantially transverse to an implant receiving end 7. In one embodiment, the implant receiving end 7 comprises a first hole 8 and a second hole 12, wherein the first hole 8 is positioned transverse to the second hole 12. Moreover, the second hole 12 is preferably dimensioned and configured to receive an implant longitudinal member 10. Furthermore, the cam member 2 is preferably dimensioned and configured to fit into the first hole 8 of the implant receiving end 7 of the body member 1.

Preferably, the base 4 fits onto the end 5 of the gripping handle portion 6 of the body 1. The other end (i.e., implant receiving end) 7 of the body 1, which is distally located from the handle end 6 where the base 4 connects, includes a hole 8 for accommodating the cam 2. The cam member 2 rotatably connects to the implant receiving end 7 of the body member 1. Generally, the lever 3 includes holes 9a, 9b, which may be aligned with the hole 8 in the body 1 and may align with the cam 2. The lever 3 connects to the cam member 2 and is rotatable with respect to the body member 1. The lever 3 preferably comprises a pair of generally parallel arms 18a, 18b that are sufficiently spaced apart to accommodate a width of the implant receiving end 7 of the body member 1, wherein rotation of the lever 3 causes rotation of the cam member 2. The body 1 is preferably formed in a unique generally curved geometric configuration. This generally curved configuration requires minimal force to be applied in order to bend the longitudinal member 10 (shown in FIGS. 6(A) through 6(C)), such as a rod, when it is inserted in the device 50. If the body were linear, then much greater force would be required to bend the longitudinal member 10.

FIGS. 2(A) through 2(D), with reference to FIG. 1, illustrate schematic diagrams of the rod bender body 1 of the rod bender device 50. FIG. 2(B) illustrates a cross-sectional view of the body 1, whereby the hole 11 located at the handle end 6 of the body for accommodating the base 4 (of FIG. 1) is shown. FIG. 2(C), which is a magnified view of the encircled area of FIG. 2(B), more particularly illustrates the hole 8 for accommodating the cam 2 and for aligning with the holes 9a, 9b of the lever 3. FIG. 2(D) illustrates an isolated view of the other end 7 (i.e., rod end) of the body 1 that is located distally from the handle end 6. The rod end 7 includes a hole 12 for receiving the longitudinal member 10 (of FIGS. 6(A) through 6(C)).

Figure 3B:
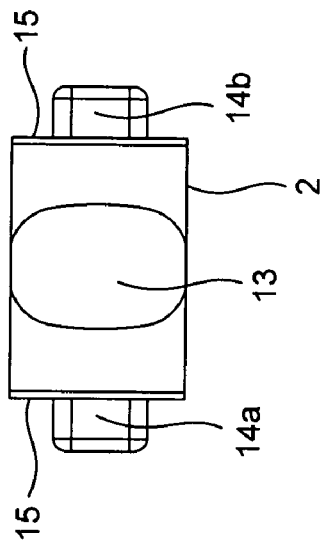
Figure 3C:
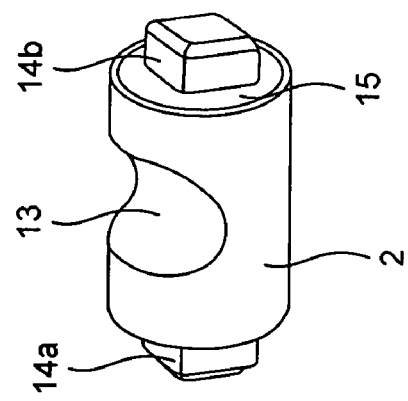
Figure 3D:
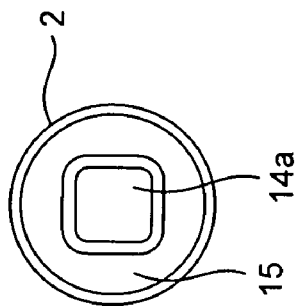

FIGS. 3(A) through 3(D), with respect to FIG. 1, illustrate schematic diagrams of the rod bender cam 2. The cam 2 generally includes an indented saddle portion 13 in the middle of the cam body 2 with a protruding peg 14a, 14b extending from each distal longitudinal end 15 of the cam body 2. The pegs 14a, 14b are dimensioned and configured to engage the respective holes 9a, 9b of the rod bender lever 3 (of FIGS. 1 and 4(A) through 4(D)). Also, the indented middle section 13 of the cam member 2 is preferably dimensioned and configured to engage the implant longitudinal member 10 (of FIGS. 6(A) through 6(C)). Furthermore, the overall shape and configuration of the cam 2 is dimensioned such that it fits into the hole 8 of the rod end 7 of the rod bender body 1 (of FIGS. 1 and 2(A) through 2(D)). FIG. 3(B) is a cross-sectional view of the cam 2.

FIGS. 4(A) through 4(C), with respect to FIG. 1, illustrate schematic diagrams of the rod bender lever 3. The lever 3 generally includes two opposite ends: a contour end 16 and an arm end 17. The contour end 16 is dimensioned and configured to allow for easy and comfortable manipulation by a user for articulating the lever 3 in various states of rotation. The arm end 17 of the lever 3 includes two arms 18a, 18b positioned parallel and apart from one another. Each arm 18a, 18b includes a respective hole 9a, 9b that accepts the respective pegs 14a, 14b of the cam 2 (of FIGS. 3(A) through 3(D)). The arms 18a, 18b are generally flexible with respect to one another. The flexure is accomplished by providing a slit 19 in the wall 20 connecting the arms 18a, 18b to each other. FIG. 4(B) is a cross-sectional view of the lever 3.

Figure 5B:
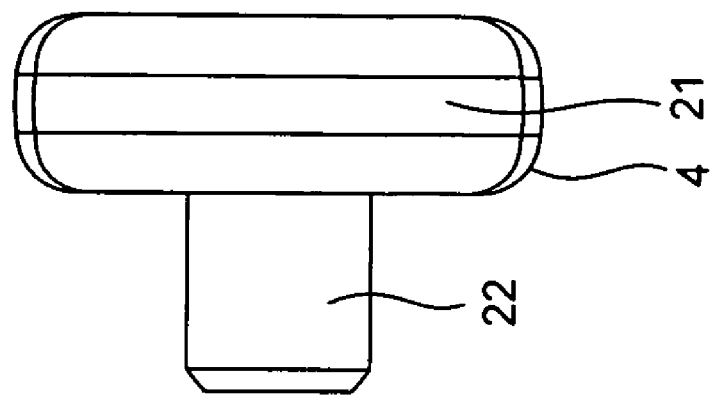
FIGS. 5(A) and 5(B) illustrate schematic diagrams of the rod bender base of the rod bender device of FIG. 1 according to an embodiment herein.
Figure 5A:
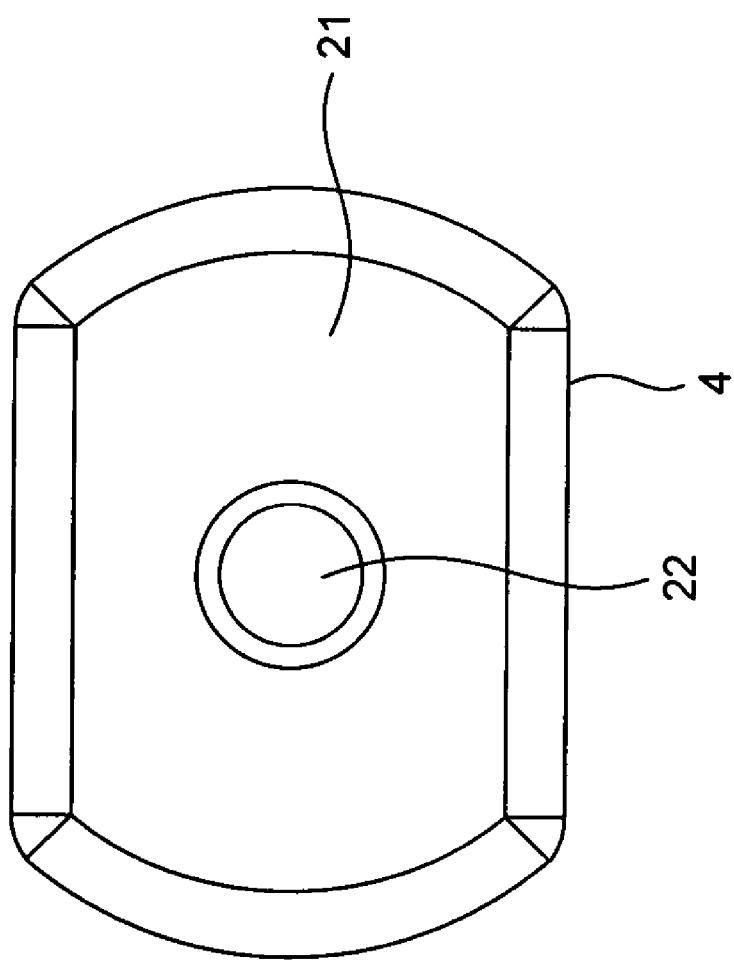

FIGS. 5(A) and 5(B) illustrate schematic diagrams of the rod bender base 4. Generally, the base 4 includes an end cap 21 having a member 22 extending away from the end cap 21. The extending member 22 is dimensioned and configured to fit into the hole 11 of the handle end 6 of the rod bender body 1 (of FIG. 2(B)). FIGS. 6(A) through 6(C) illustrate schematic diagrams of a completed rod bender device 50 (left side 30a and right side 30b) manipulating and bending a longitudinal member (such as a rod) 10 according to an embodiment herein. Generally, FIG. 6(A) illustrates the rod bender device 50 with the rod 10 loaded into the rod end 7 of the rod bender body 1 and ready to be bent. FIGS. 6(B) and 6(C) illustrate the rod bender device 50 bending the rod 10 in various degrees of bending.

Figure 7A:
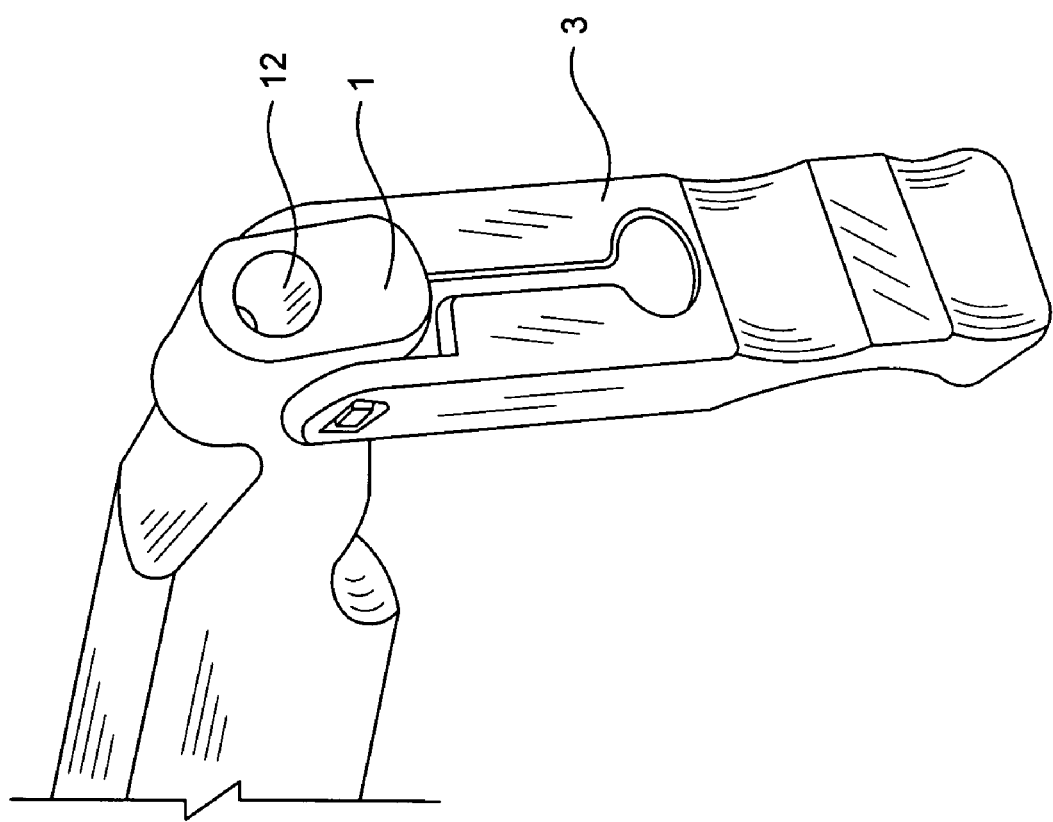
FIG. 7(A) illustrates a schematic diagram of the rod bender device of FIG. 1 in an open position according to an embodiment herein.
Figure 7B:
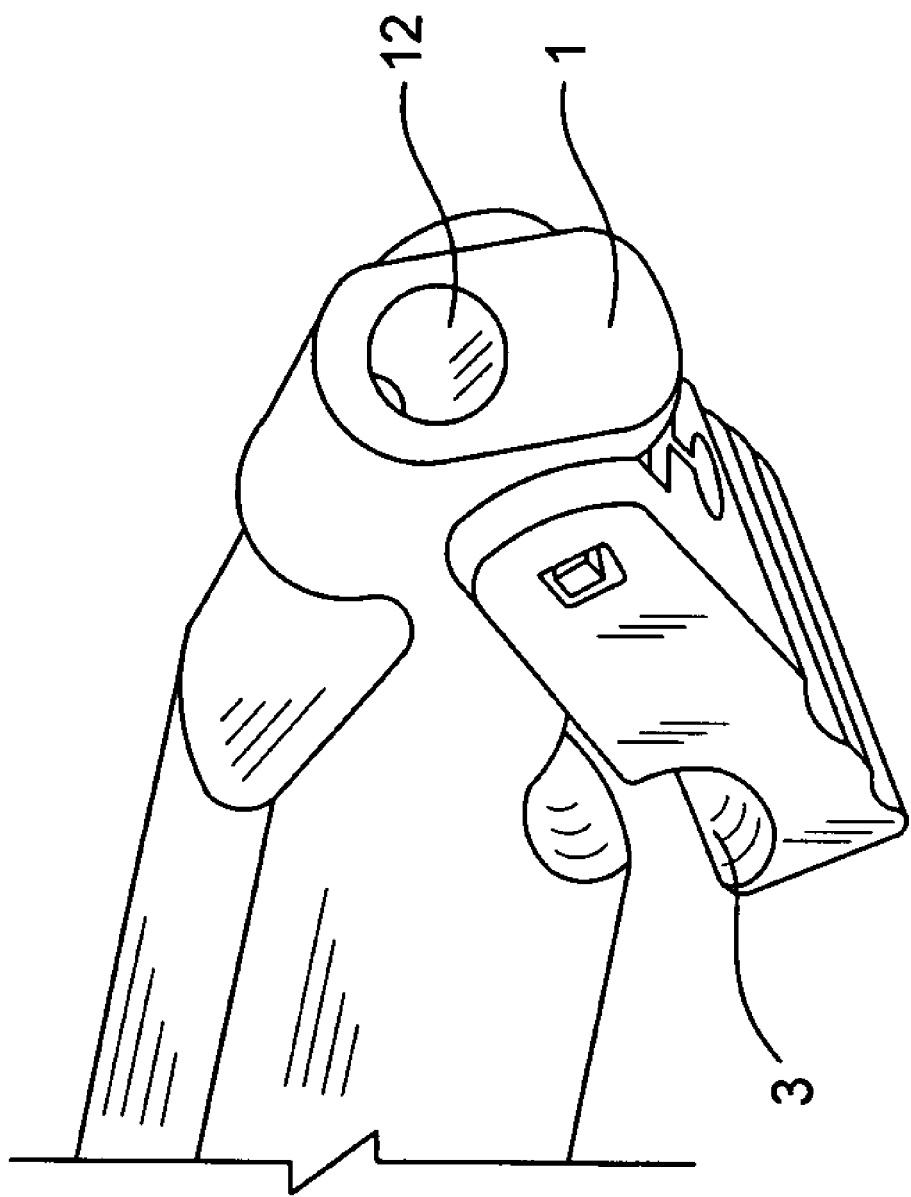
FIG. 7(B) illustrates a schematic diagram of the rod bender device of FIG. 1 in a closed position according to an embodiment herein.
Figure 8:
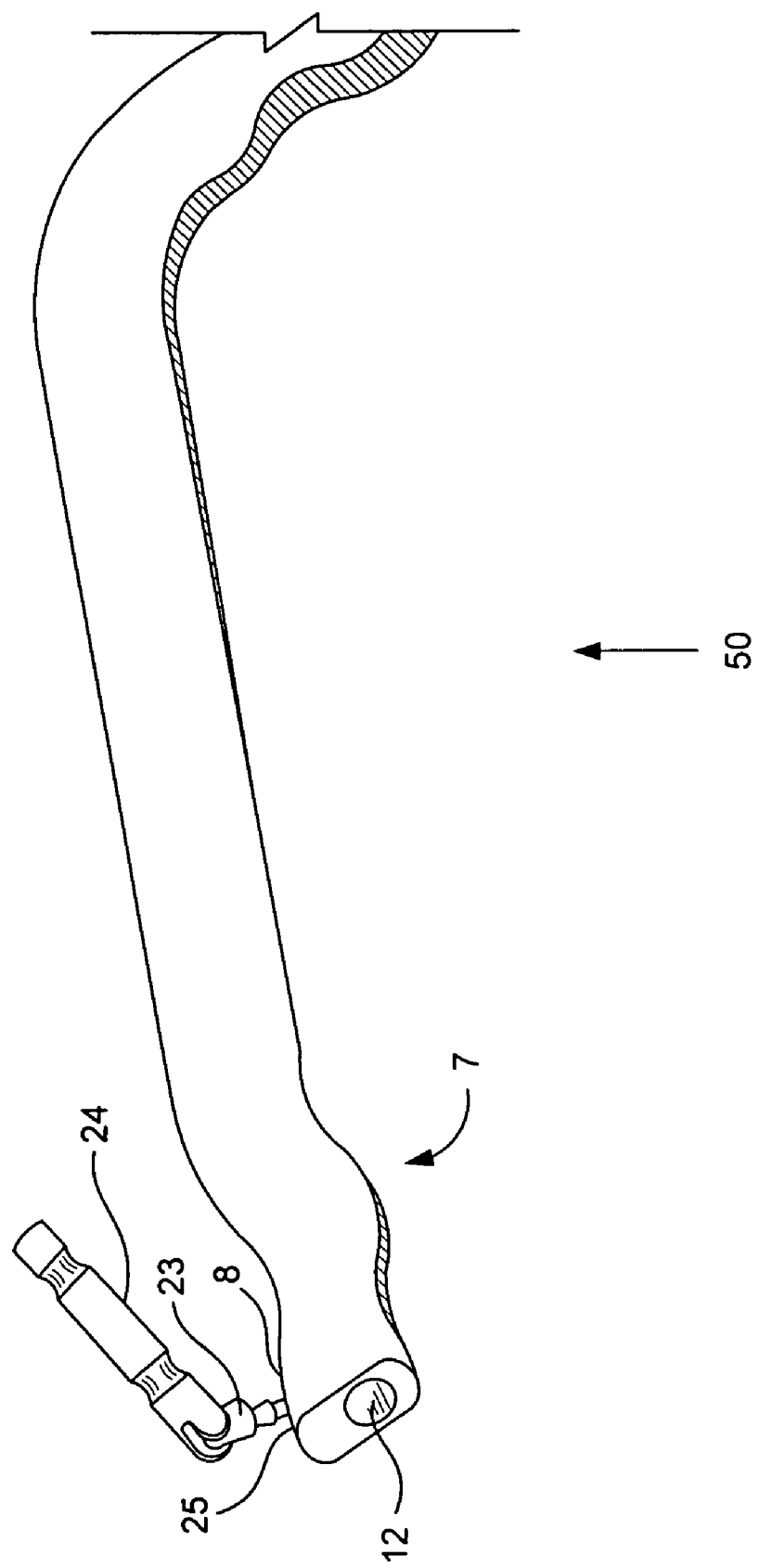
FIG. 8 illustrates a schematic diagram of a rod bender device with a screw-like feature according to an alternative embodiment herein.

FIG. 7(A) illustrates a schematic diagram of the rod bender device 50 in an open position according to an embodiment herein. This view illustrates the hole 12 in the rod end 7 of the rod bender body 1 (of FIG. 1) which accommodates a rod 10 (of FIGS. 6(A) through 6(C)). FIG. 7(A) also illustrates the lever 3. FIG. 7(B) illustrates a schematic diagram of the rod bender device 50 in a closed position according to an embodiment herein. When the lever 3 is closed, it engages the cam 2 to lock the rod 10 (of FIGS. 6(A) through 6(C)) into place. FIG. 8 illustrates a schematic diagram of a rod bender device 50 with a screw-like feature 23 according to an alternative embodiment herein. The screw-like feature 23, which connects to a rotating handle 24 allows for the locking of the rod 10 (not shown in FIG. 8) into place into the rod end 7 of the rod bender body 1 without the need for a cam 2. In such an embodiment, the hole 8 of the rod bender body 1 is preferably configured on an upper side 25 of the rod end 7 of the rod bender body 1, wherein the hole 8 is configured with screw-like mating features capable of engaging the screw-like feature 23, which then connects to the handle 24. Moreover, in this embodiment the handle 24 may be configured similar to lever 3 or it may be configured in a cylindrical fashion or any other suitable configuration. Preferably, the handle 24 attaches to the screw-like feature 23 in such a manner as to provide suitable torque for rotating the screw-like feature 23 into hole 8 in order to secure the rod 10 firmly into place prior to bending. In the second embodiment, the hole 12, which accommodates the rod 10 (not shown in FIG. 8) is preferably configured in a similar manner as in the first embodiment.

Figure 9:
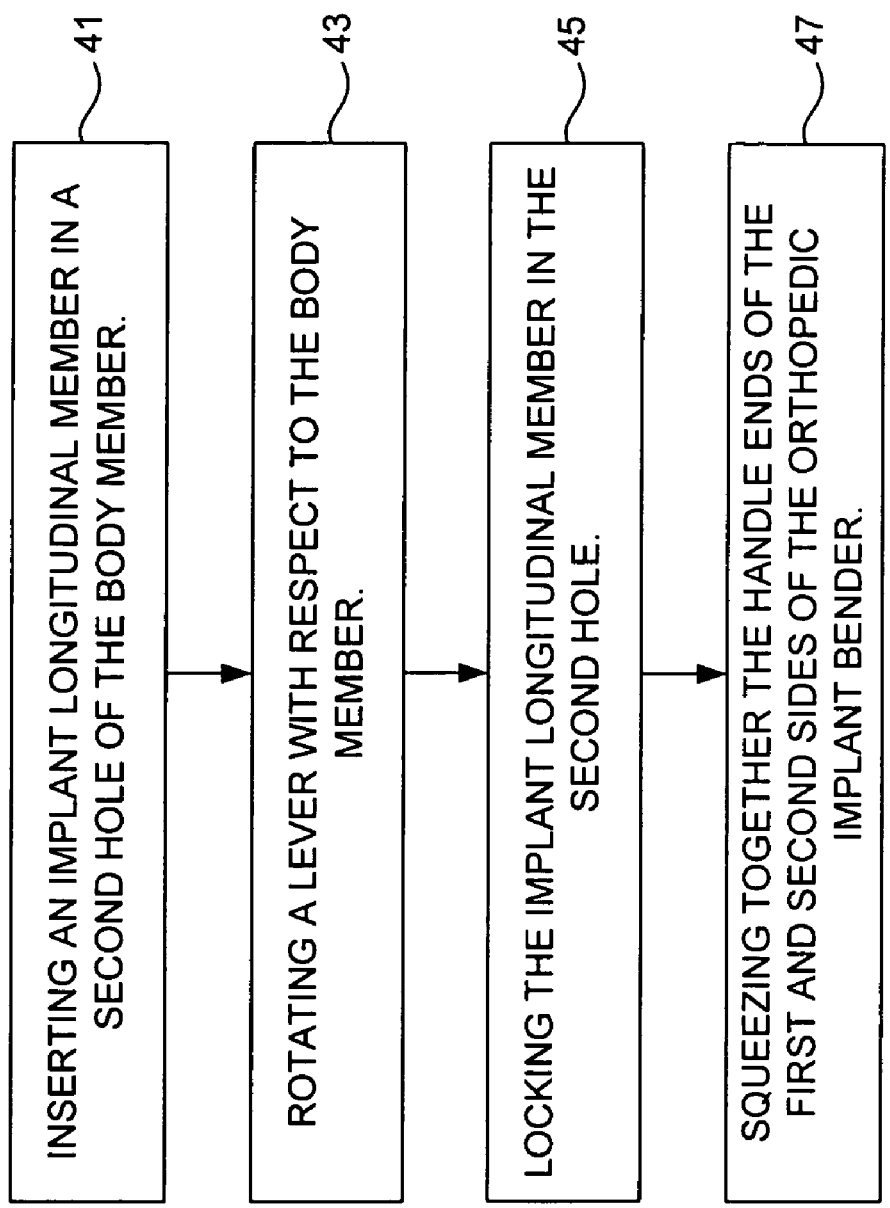
FIG. 9 is a flow diagram illustrating a preferred method according to an embodiment herein.

FIG. 9, with reference to FIGS. 1 through 8, is a flow diagram illustrating a method of bending an implant longitudinal member 10 in an orthopedic implant bender 50 comprising a first side 30a and a second side 30b, wherein each of the first side 30a and the second side 30b comprises a curved body member 1 comprising a handle end 6 and an implant receiving end 7, wherein the implant receiving end 7 comprises a first hole 8 and a second hole 12; a cam member 2 rotatably connected to the body member 1; and a lever 3 connected to the cam member 2; wherein the method comprises inserting (41) the implant longitudinal member 10 in the second hole 12; rotating (43) the lever 3 with respect to the body member 1, wherein rotation of the lever 3 causes rotation of the cam member 2; locking (45) the implant longitudinal member 10 in the second hole 12; and squeezing (47) together the handle ends 6 of the first and second sides 30a, 30b of the orthopedic implant bender 50, wherein the squeezing (47) causes the implant longitudinal member 10 to bend, wherein a curved configuration of the body member 1 preferably requires a minimal force to be applied to the handle end 6 of the body member 1 in order to bend the implant longitudinal member 10.

Generally, the method of bending a rod 10 according to an embodiment herein includes inserting a rod 10 into a one side, for example, the left side rod bender 30a, at a minimum of 10 mm of the rod length and closing the lever 3 to firmly grip the rod 10. This process is repeated on the other side of the rod with the right side rod bender 30b. Next, force is exerted on the grooved handle portion 6 at the other end of the rod benders to bend and contour rod 10. The resulting radius is preferably uniform between the two rod benders (left side and right side 30a, 30b) and is free of notches that may cause premature failure in titanium rods, which are the most widely used materials in spinal surgeries. To release the rod 10 from the instruments, a user simply has to pull back on the levers 3 of the rod benders 30a, 30b and remove the rod 10.

The rod bender device 50 provided by the embodiments herein may be used to contour a spinal rod 10 to fit optimally in two or more bone anchors (not shown). The rod bender device 50 preferably creates one constant radius of any reasonable size between the left and right side rod benders 30a, 30b. The cam mechanism 2 provided by the embodiments herein is dimensioned and configured to firmly grip multiple diameter rods firmly while causing minimal rod notching.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A two-handed orthopedic implant bender apparatus comprising:
    a longitudinal member;
    a first bender; and
    a second bender identically configured to said first bender, wherein said first bender and said second bender bend said longitudinal member in tandem, and wherein each of said first bender and said second bender comprises:
        a curved body member comprising a handle end and an implant receiving end;
        an exactly one-piece cam member rotatably connected to said implant receiving end of said body member, wherein said cam member comprises an indented middle section and a peg extending from each distal longitudinal end of said cam member; and
        an exactly one-piece lever connected to said cam member and rotatable with respect to said body member, wherein said lever comprises a pair of generally parallel arms sufficiently spaced apart to accommodate an entire width of said implant receiving end of said body member,
        wherein rotation of said lever causes rotation of said cam member.

2. The apparatus of claim 1, wherein said implant receiving end comprises a first hole and a second hole, and wherein said first hole is transverse to said second hole.

3. The apparatus of claim 2, wherein said second hole receives said longitudinal member such that said cam member is positioned below said longitudinal member.

4. The apparatus of claim 2, wherein said cam member fits into said first hole of said implant receiving end of said body member.

5. The apparatus of claim 1, wherein said lever further comprises a pair of through holes in each of said arms, and wherein said through holes attach to said peg.

6. The apparatus of claim 1, wherein said indented middle section of said cam member engages said longitudinal member.

7. The apparatus of claim 1, wherein a curved configuration of said body member requires a minimal force to be applied to said handle end of said body member in order to bend said longitudinal member.

8. The apparatus of claim 1, further comprising a base member connected to said handle end of said body member.

9. The apparatus of claim 1, wherein said arms are flexible with respect to one another.

10. The apparatus of claim 9, wherein said lever further comprises a wall connecting said arms to each other, and wherein said wall comprises a slit.

11. The apparatus of claim 1, wherein said lever further comprises a contoured end positioned opposite to said arms.

12. A method of bending an implant longitudinal member in a two-handed orthopedic implant apparatus comprising said implant longitudinal member; a first bender; and a second bender identically configured to said first bender, wherein each of said first bender and said second bender comprises a curved body member comprising a handle end and an implant receiving end, wherein said implant receiving end comprises a first hole and a second hole; an exactly one-piece cam member rotatably connected to said body member, wherein said cam member comprises an indented middle section and a peg extending from each distal longitudinal end of said cam member; and an exactly one-piece lever connected to said cam member, wherein said lever comprises a pair of generally parallel arms sufficiently spaced apart to accommodate an entire width of said implant receiving end of said body member, said method comprising:
  inserting said implant longitudinal member in said second hole;
  rotating said lever with respect to said body member, wherein rotation of said lever causes rotation of said cam member;
  locking said implant longitudinal member in said second hole; and
  squeezing together the handle ends of the first and second benders of said orthopedic implant bender, wherein said squeezing causes said implant longitudinal member to bend,
  wherein said first bender and said second bender bend said longitudinal member in tandem.

13. The method of claim 12, wherein a curved configuration of said body member requires a minimal force to be applied to said handle end of said body member in order to bend said implant longitudinal member.

14. An orthopedic implant bender apparatus comprising:
  an implant longitudinal member;
  a first bender; and
  a second bender, wherein each of said first bender and said second bender comprises:
    a curved body member comprising a handle end and an implant receiving end, wherein said implant receiving end receives said longitudinal member, wherein said implant receiving end comprises a first hole and a second hole, and wherein said first hole is transverse to said second hole;
    a single piece cam member rotatably connected to said implant receiving end of said body member, wherein said cam member is positioned below said implant longitudinal member, and wherein said cam member comprises an indented middle section and a peg extending from each distal longitudinal end of said cam member; and
    a single piece lever connected to said cam member and rotatable with respect to said body member, wherein said lever comprises a pair of generally parallel arms sufficiently spaced apart to accommodate a width of said implant receiving end of said body member,
    wherein rotation of said lever causes rotation of said cam member.

15. The implant bender apparatus of claim 14, wherein said second hole receives said implant longitudinal member.

16. The implant bender apparatus of claim 14, wherein said cam member fits into said first hole of said implant receiving end of said body member.

17. The implant bender apparatus of claim 14, wherein said lever further comprises a pair of through holes in each of said arms, and wherein said through holes attach to said peg.

18. The implant bender apparatus of claim 15, wherein said indented middle section of said cam member engages said implant longitudinal member.

19. The implant bender apparatus of claim 14, further comprising a base member connected to said handle end of said body member.

20. The implant bender apparatus of claim 14, wherein said lever further comprises a wall connecting said arms to each other, and wherein said wall comprises a slit.

* * * * *

UNITED STATES PATENT AND TRADEMARK OFFICE
CERTIFICATE OF CORRECTION

PATENT NO. : 7,488,331 B2
APPLICATION NO. : 11/280013
DATED : February 10, 2009
INVENTOR(S) : Mahmoud F. Abdelgany It is certified that error appears in the above-identified patent and that said Letters Patent is hereby corrected as shown below:

On the Title page, next to the listing for the Assignee [73]: please delete "Custon Spine, Inc." and in its place, please insert --Custom Spine, Inc.--

Signed and Sealed this

Thirty-first Day of March, 2009

JOHN DOLL
*Acting Director of the United States Patent and Trademark Office*